United States Patent [19]

Serres

[11] Patent Number: 5,043,289

[45] Date of Patent: Aug. 27, 1991

[54] METHOD AND DEVICE FOR ASSAYING IMMUNOLOGICALLY REACTIVE SUBSTANCES OF CLINICAL INTEREST

[76] Inventor: Pierre F. Serres, 4 rue Etienne Radix, 69630 Chaponost, France

[21] Appl. No.: 102,739

[22] Filed: Sep. 30, 1987

[30] Foreign Application Priority Data

Sep. 30, 1986 [FR] France ................. 86 13782

[51] Int. Cl.⁵ ........................................... G01N 33/546
[52] U.S. Cl. ................................... 436/534; 436/518; 436/523; 436/531; 436/805
[58] Field of Search ............... 436/805, 518, 523, 521, 436/534

[56] References Cited

U.S. PATENT DOCUMENTS

| | | | |
|---|---|---|---|
| 3,488,156 | 1/1970 | Good et al. ........................... 23/253 |
| 4,203,724 | 5/1980 | Sawai ................................. 436/805 X |
| 4,205,954 | 6/1980 | Babson ............................... 436/805 X |
| 4,239,746 | 12/1980 | Bartos et al. ........................ 424/12 |
| 4,250,394 | 2/1981 | O'Connor ............................ 250/574 |
| 4,398,894 | 8/1983 | Yamamoto .......................... 436/517 |
| 4,446,239 | 5/1984 | Tsuji ................................... 436/805 X |
| 4,454,233 | 6/1984 | Wang .................................. 436/525 |
| 4,521,521 | 6/1985 | Abbott ............................... 436/805 X |
| 4,554,257 | 11/1985 | Aladjem ............................. 436/805 X |
| 4,556,641 | 12/1985 | Kano .................................. 436/805 X |
| 4,760,030 | 7/1988 | Peterson ............................ 436/805 X |

FOREIGN PATENT DOCUMENTS

| | | |
|---|---|---|
| 0005978 | 12/1979 | European Pat. Off. . |
| 0094216 | 11/1983 | European Pat. Off. . |
| 0106122 | 4/1984 | European Pat. Off. . |
| 0163312 | 12/1985 | European Pat. Off. . |
| 0174195 | 3/1986 | European Pat. Off. . |
| 0186946 | 7/1986 | European Pat. Off. . |
| 2040441 | 8/1980 | United Kingdom . |
| 2136565 | 9/1984 | United Kingdom . |

*Primary Examiner*—Christine Nucker
*Attorney, Agent, or Firm*—Parkhurst, Wendel & Rossi

[57] ABSTRACT

A method and device of quantitatively assaying an immunologically reactive substance of clinical interest, wherein the method includes the steps of grafting an immunologically active substance onto natural or synthetic microparticles, agglutinating the microparticles in a liquid medium in the presence of an immunologically reactive substance of clinical interest, and optically measuring the agglutinated substances to determine the assay of the immunological reactive substance of clinical interest. The device employed for carrying out the above method includes a first series of tubes which contain at least one freeze-dried calibration range of the substance to be assayed, a second series of tubes which contain an immunological active substance acting as the assaying agent, and a third series of small tubes containing a freeze-dried specimen of the dilution solution of the calibration range.

10 Claims, 6 Drawing Sheets

METHOD AND DEVICE FOR ASSAYING IMMUNOLOGICALLY REACTIVE SUBSTANCES OF CLINICAL INTEREST

BACKGROUND OF THE INVENTION

1. Field of the Invention

The present invention relates to a method of assaying immunologically reactive substances of clinical interest. It also relates to a device for implementing this method.

2. Description of the Prior Art

Immunologically reactive substances means chiefly all the antigens (including the haptens) and the antibodies (monoclonal or polyclonal) produced by cell fusion, or by natural or induced immunization.

Immunologically reactive substances of clinical interest means chiefly all the antigen or antibody molecules whose assay in a biological specimen of human or animal origin may be of interest in medical diagnostics, clinical research or the monitoring of a pathological process or of a therapy which is employed.

The immunological phenomenon of which use is made in these immunoassay methods is shown in FIG. 1.

The most widely employed assay methods based on the use of the curve in FIG. 1 are:

radial immunodiffusion, radioimmunology, immunoenzymology, immunofluorescence; and nephelometry.

Furthermore, some attempts at quantitative versions of the "latex immunotest", namely the agglutination of synthetic microspheres, have been described over a number of years. Until now, these techniques, which have been employed widely and for a long time (J. M. Singer and C. M. Plotz, The Latex fixation test, American Journal of Medicine 21, 888 (1956)), because of their simplicity and their low cost, were only qualitative (strip) or semiquantitative (well) in their form. The qualitative (strip) or semiquantitative forms (strip—sheet—well) of the Latex immunotest continue, furthermore, to be widely employed in clinical diagnostics at the present time and are the subject of many patents and publications, especially in the field of virology and microbiology (R. F. Khabbaz, H. C. Standford et al, 1985, Measurement of amikacin in serum by a Latex agglutination inhibition test, Journal of Clinical Microbiology, 22: 699–701, U.S. Pat. No. 3,488,156, European Patent Application 186 946). In these screening or detection techniques, the antigen or antibody is fixed on synthetic microspheres and the absence or presence of agglutination by the corresponding antigen or antibody is assessed in a tube or in a well, visually or by turbidimetry.

The few quantitative attempts at a Latex immunotest which are proposed in the literature (for example J. P. Ripoll, A. M. Roch, G. A. Quash and J. Grange, 1980, Journal of Immunological Methods 33, 159–173, European Patent Applications 189 389 and 5978) involve substantially three stages:

Stage I: Stage of fixing the antigen or the antibody on a micrometer of synthetic polymer, between 0.01 micrometer and 5 micrometers in size. The fixing is performed by any known means, which are identical with those described in the strip techniques (for example U.S. Pat. No. 4,217,338).

Stage II: Stage of immunological agglutination of the synthetic microspheres carrying the antigen or the antibody. This stage II of the method, namely the immunological agglutination of the synthetic microspheres, should aim at two objectives:

(1) the maximum reduction in the nonspecific agglutination of the particles; nonspecific agglutination means the agglutination of the particles which is due to weak interactions (of the hydrogen bond, ionic or van der Waals type), between the microspheres or the proteins which are fixed on the latter, (2) the maximum increase in specific (immunological) agglutination of the particles.

During this stage, substantially chemical or biochemical means are employed to stabilize the particles, in order to reduce nonspecific agglutination to a minimum.

During this stage, means are also employed in order to increase the specific agglutination of the particles, and consequently the accuracy of the assay.

To reduce the nonspecific agglutination of the particles, U.S. Pat. No. 4,329,152 proposes to stabilize them by fixing bovine albumin made electronegative at a pH which is substantially equal to 10. The highly basic pH imposed in this manner on the reactant and on the calibration ranges is incompatible with survival of the proteins, and makes it a reactant which is difficult to employ. Furthermore, the reliability of the method is reduced thereby, because buffer solutions at pH values as basic as this are highly unstable. Furthermore, the bovine albumin fixed by hydrophobic bonding separates progressively from the particles at pH 10, and progressively loses its stabilizing capacity.

Unfortunately, the chaotropic agents which are sometimes employed to reduce the nonspecific agglutination of the particles have the disadvantage of weakening or breaking the antigen-antibody bonds.

Other stabilizing methods which are highly complicated and which cannot be employed in an industrial reactant make use of mixtures of heavy and light particles (ex: European Patent 163 312) and of centrifuging operations.

In order to promote the specific agglutination of the particles, that is to say immunological agglutination, the methods described employ conventional agitation, at a constant temperature in a water bath at 37° C. or 40° C., for periods ranging from one half hour to one hour. Such periods of incubation at 37° C., in addition to promoting the undesirable nonspecific agglutination of the particles, demand strict and painstaking stopwatch timing of the initial introduction of the reactant into each tube in the series, and of the process of interrupting the reaction in the series of tubes.

An increase in the specific (immunological) agglutination of the particles is sometimes practiced by adding to the reaction medium additives such as, for example, dextrose, known under the trademark "Dextran" or polyethylene glycol. The disadvantage of these substances is that frequently they are to a large extent hydrophobic, and therefore they attach themselves to the Fc fragments of the antibodies fixed on the microparticles, fragments which are themselves highly hydrophobic, thus producing a nonimmunological agglutination of the particles, and thereby inducing interferences and, ipso facto, false positive reactions.

Stage III: Stage of reading the result.

At the present time the techniques of reading the result of the agglutination in quantitative latex immunotests are:

particle counting, opacimetry, also known as turbidimetry (sometimes carried out in the visible or the infrared, in most cases in the near infrared), laser nephelometry, and centrifugal analysis.

Laser nephelometry measures the light scattered by aggregates of latex particles. This technique, described, for example, in the following article: J. Grange, A. M. Roch and G. A. Quash, 1977, Journal of Immunological Methods 18, 326–375, introduces the disadvantage of requiring a costly and sophisticated reading apparatus.

Particle counting, described, for example, in the following article: C. G. Magnusson, P. L. Masson, Journal of Allergy Clin. and Immunol. 70: 326, 1982, also requires a complex and costly apparatus, accessible to only a few laboratories.

Opacimetry in the visible, also called turbidimetry in the visible, measures the light transmitted by the particle suspension, that is to say the light which is neither absorbed by the particles nor scattered by the latter. The opacimetry or turbidimetry of the latex immunotests, whether qualitative or quantitative, must be performed at a wavelength which lies fairly close to the particle size. Validity of the turbidimetric measurement calls for highly dilute suspensions, in order to enable the desired screening effect to be seen and, as indicated in the Certificate of Addition no 78/28,250 to french patent no 77/25,049, in order to reduce the absorption of light by the particles to a minimum.

Depending on the particle size, turbidimetric (or opacimetric) measurements in the visible of the latex immunotests described in the literature (example: A. M. Bernard, R. R. Lauwerys, 1982, clinica Chemica Acta 119, 335–339) employ various wavelengths in the visible, for example 360, 400, 450 and, much more widely, between 600 and 750 nanometres. The precision of the turbidimetric results is mediocre because the particle suspensions must be very dilute in order, as already stated, to produce the desired screeen effect variations and in order to reduce the absorption by the latices to a minimum. Furthermore, in order to increase the precision of the result, reading cells in which the optical path is long, of the order of two to four centimeters, must be generally employed in these techniques.

In order to employ more concentrated latex suspensions and thus to increase the precision of the assays, and in order to be free from interference by the absorption of the latices in the visible or in the ultraviolet, French Patent FR-A-77/25,049 and its Certificate of Addition FR-A-78/28250 recommend infrared opacimetry for particle reading. In point of fact, latices no longer absorb light in the infrared. The disadvantage of this technique is that it calls for costly and sophisticated apparatus for infrared opacimetric reading.

SUMMARY OF THE INVENTION

The primary objective of the present invention is therefore to overcome the numerous disadvantages of the stages II and III emphasized above.

With respect to the Stage II techniques discussed above, one of the objectives of the present invention is to eliminate the nonspecific agglutination of the particles and simultaneously to increase the specific immunological agglutination of the particles, without introducing all the disadvantages described above, and, what is more, with a considerable shortening of the duration of the operation.

Another object of the present invention is the implementation of an agglutination method and apparatus which is simple to use, and very fast.

Another object of the present invention is the implementation of a method of reading the result which is also simple and very fast, and within the reach of any laboratory. The objectives of the present invention are reached by a method for assaying immunologically reactive substances of clinical interest of the type in which:

an immunologically active substance acting as the assay reactant is grafted beforehand onto the microparticules, the said microparticles are agglutinated by means of the immunologically reactive substance of clinical interest, the result produced by the agglutination reaction, which is compared with a calibration range, is measured by reading.

The assay method according to the invention is characterized in that the agglutination stage is performed by subjecting the grafted microparticles to a periodic motion at a frequency of between 4 and 40 Hertz, and with an amplitude ranging from a few millimeters to a few centimeters.

It has been found, in fact, that when the frequency is less than 4 Hertz, the advantage of the method was reduced because the duration of the agglutination stage is increased in order to produce a usable result and because the required effect on the nonspecific agglutination becomes mediocre; on the other hand, when the frequency is higher than 40 Hertz, breakup of the aggregates (immunocomplexes) formed by the agglutinated microparticles is produced. As it is apparent from the above description, in the agglutination stage (stage II of the method), in order to overcome all the disadvantages of the chemical methods described above, aiming at reducing the nonspecific agglutination of the particles, or increasing the immunological agglutination thereof, the agglutination means used according to the invention employs a mechanical method which simultaneously meets both these objectives. This mechanical method is based on the observation that nonspecific agglutination, which is associated with weak interactions between the particles (bonds of ionic, hydrogen or Van der Waals type) is rendered impossible or is greatly inhibited by a periodic motion imparted to these, of very low amplitude and very high frequency, whatever the trajectory of the periodic motion (for example and conveniently rectilinear, circular or ovalized). It has also been shown that a method of this kind markedly promotes the specific (immunological) agglutination of the microparticles carrying the corresponding antigen or antibody, and hence permits a rapid specific reaction which, moreover, is carried out at ambient temperature.

The present invention also proposes a method for assaying immunologically reactive substances of clinical interest of the type in which:

an immunologically active substance acting as the assay reactant is grafted beforehand onto the microparticles, the microparticles are agglutinated by means of the immunologically reactive substance of clinical interest, and the result produced by the agglutination reaction, which is compared with a calibration range, is measured by reading, characterized in that the stage of reading the result is performed:

(1) firstly, by determination of the absorption maximum by the particles of ultraviolet and visible light of a suspension in a liquid medium of nonagglutinated microparticles, the determination being performed by obtaining the ultraviolet and visible absorption spectrum of the said suspension, the wavelength corresponding to the absorption maximum being called λmax, (2) then by reading the result, by means of ultraviolet and visible absorption spectrophotometry, operating in the vicinity of the said wavelength λmax, determined earlier, after the immunological agglutination reaction and a dilution of the incubation medium performed in a known manner.

It is surprising, especially when the microparticles are latices, that it is possible to perform this stage of reading using ultraviolet and visible absorption of the latex particles, given that the above mentioned Certificate of Addition FR-A-78/28,250 describes this phenomenon as a major disadvantage. It seems that, in the method of reading according to the invention, it is the actual absorption of the ultraviolet and visible light by the particles themselves which is utilized, and this constitutes a new step. In fact, the turbidimetric (opacimetric) methods measure only an "apparent absorption" of the particles suspension, that is to say actually the light which is not absorbed by the particles.

In fact, it has been observed, and this is one of the characteristics of the invention, that a microparticle capable of absorbing ultraviolet and visible light and whose size can vary between 0.01 and 5 micrometers, of synthetic polymer, whatever its size and its chemical nature may be (for example: polystyrene, polyvinyltoluene, acrylonitrile, styrene-butadiene, acrylonitrile-acrylic acid copolymers, acrylic ester, polyvinylbutadiene), has a characteristic maximum of absorption of ultraviolet and visible light with an extinction coefficient which depends on the wavelength. In addition, it has been shown, and this observation is employed in the method of reading according to the invention, that if a measurement is carried out on a suspension in a liquid medium of these nonagglutinated microparticles, using absorption spectrophotometry at the wavelength λmax corresponding to the maximum absorption of ultraviolet and visible light by the nonagglutinated microparticles (λmax being characteristic of a given microparticle), the result is not at all or very weakly effected by the presence of aggregates (or agglutinates) of these same microparticles in the medium, because the aggregates of these microparticles, whatever their size, no longer absorb ultraviolet and visible light at this λmax, their absorption maxima being far from the λmax defined earlier.

Furthermore, it has been shown that a spectrophotometric measurement of ultraviolet and visible absorption of a suspension in a liquid medium of the said nonagglutinated (monomeric) microparticles obeys the Beer-Lambert law, and does so even at very high particle concentrations, and this gives it a clear advantage in relation to the principle of turbidimetric measurements, which calls for very dilute suspensions.

Advantageously, in practice:

the trajectory of the periodic motion may be of any kind, but is preferably circular, rectilinear or ovalized, the agglutination stage is performed at ambient temperature, the duration of the periodic motion imparted to the microparticles during the agglutination stage is a function of the frequency of the vibration, of the trajectory and of the amplitude of the motion. It is advantageously 10 minutes for a frequency of 20 hertz and a periodic circular motion 4 millimeters in diameter, the microparticles suitable for the spectrophotometric reading of ultraviolet and visible absorption consist of natural or synthetic materials, of any absorbing nature, especially polystyrene, polyvinyltoluene, acrylonitrile, styrene-butadiene, acrylonitrile-acrylic acid copolymers, acrylic ester and polyvinylbutadiene copolymers, and preferably polystyrene, the microparticles are of any shape, but are preferably in the form of microspheres, the diameter of the natural or synthetic microspheres is between 0.01 and 5 micrometers, and preferably close to 0.8 micrometers, the microparticles consist of an absorbing but colorless material, it is also possible to use absorbing microparticles which are colorless. In this case, the spectrophotometric reading of the result by ultraviolet and visible absorption spectrophotometry is performed either at a wavelength corresponding to the absorption maximum of the material of the nonagglutinated particles, or at the wavelength corresponding to the absorption maximum of the color of the particle in question.

The invention also relates to a device for implementing the method characterized in that it comprises at least:

a first series of tubes containing at least one freeze-dried calibration range of the substance to be assayed, a second series of tubes containing an immunologically active substance and acting as the assaying agent, grafted onto the microparticles, the suspension referred to as "reactant" being in an liquid phase ready for use, the concentration in weight of the microparticles being comprised between 0.1 and 10 per cent a third series of tubes containing a freeze-dried specimen of the dilution solution of the calibration range, The manner in which the invention may be implemented and the advantages which stem therefrom will become more apparent from the example of embodiment which follows, given by way of guidance and without any limitation, in support of the attached figures.

DETAILED DESCRIPTION OF THE PREFERRED EMBODIMENTS

Figure 1:
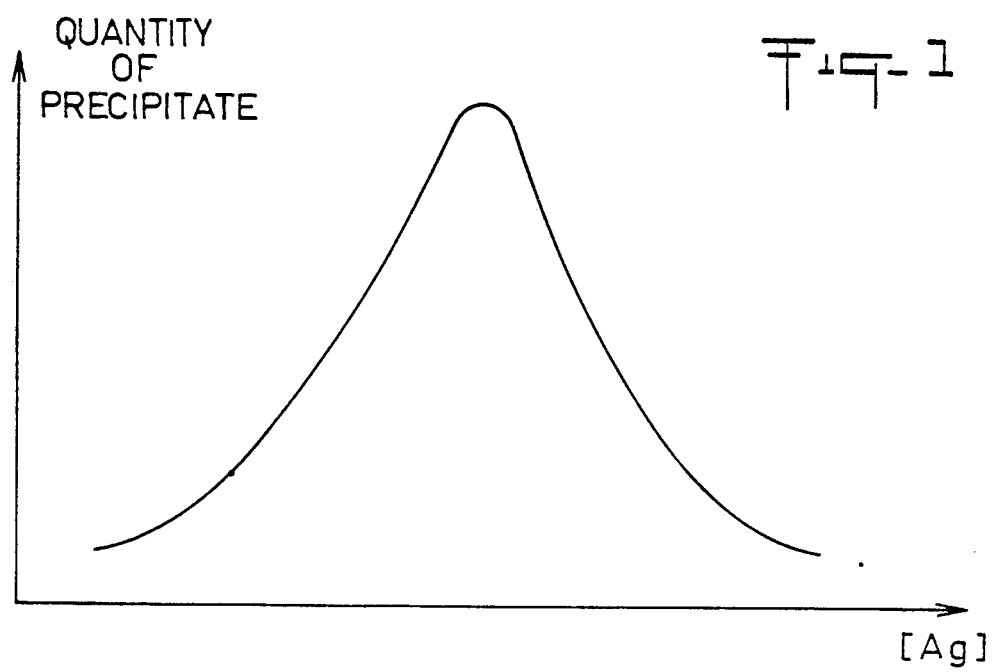
FIG. 1 is a diagram illustrating the immunological phenomenon of which use is being made.

The example which follows corresponds to the assay of antigens by means of antibodies grafted onto microspheres. It is obvious that it would be equally possible to assay antibodies by means of antigens by following the same procedure but by replacing the antigens by the antibodies and vice versa.

Before the assay as such, the antibodies are first grafted onto graded synthetic microspheres, also called a latex. These are made, for example, of polystyrene, polyvinyltoluene, acrylonitrile, styrene-butadiene, acrylonitrile-acrylic acid copolymer, acrylic ester, polyvinyl butadiene, and the like. For example, the particles of latices K 140, K 109, K 160, ψ512, ψ513, ψ480, ψ502 (—COOH) or ψ169, ψ181 (—CONH2), sold under these trade names by Rhône-Poulenc, are very highly suitable for the method.

The grafting of the antibodies onto the synthetic microspheres is performed in a known manner, that is to say by ionic, hydrophobic or covalent fixation.

When use is made of attachments of an ionic or hydrophobic type between the antibodies and the latex microspheres, these attachments, which are produced in a known manner merely by bringing the protein and the support together, lead to phenomena of detachment of the proteins from the support (also referred to as salting out). One of the reasons for the salting-out phenomena is that continual exchanges take place between the population of antibodies of the immuno-gamma-globulins G type fixed in this manner and the population of the said immuno-gamma-globulins G which is frequently present in the specimen to be analyzed.

Advantageously, the covalent fixation methods are more reliable and are preferable in this type of method of immunoassay. Methods of covalent fixation of antibody or of antigen onto the synthetic microspheres, or latex, are well known, so that there is no need to describe them here further in detail.

In the method according to the invention, when a fixation of the covalent type is employed, use is advantageously made of a fixation method which has never been described in an application of this type, and which yields good results.

According to this coupling method, the functional radicals present on the microspheres and called into action are chiefly the following: —COOH, —CONH2, —CONH—NH2 and —COOCH3.

These radicals are converted into acyl azides (—CON3) by the method which will be described, the azide reacting with the —NH2, —SH or —OH radicals of the biological molecules (antigens or antibodies) which it is intended to graft.

For example, the latices ψ169 and ψ181 are first treated with hydrazine in solution and then with the vapor of acidic sodium nitrite, under mild conditions, before being brought into contact with a poly-L-lysine-antibody mixture. The carboxylated latices ψ480 or ψ502 are carboxymethylated with acidic methanol, and then treated with hydrazine in solution, and then with vapor of acidic sodium nitrite under mild conditions, before being grafted in an appropriate ratio with a poly-L-lysine-antibody mixture.

EXAMPLE

Grafting of human anti-immuno-gamma-globulin G antibodies and human anti-B2-microglobulin onto microspheres of polystyrene ψ480 and 502 (Rhône-Poulenc) with diameters of 0.8 and 0.85 micrometers respectively.

This grafting takes place in accordance with various stages, summarized below:

methylation of the latex carboxyl groups: esterification of the free carboxyls of the latices is performed in a bath of acidified methanol for a minimum of three days and a maximum of ten days, the saturation plateau being generally at an average of five days, vigorous rinsing with water, treatment of the carboxymethylated latices with hydrazine for 1 to 15 hours with stirring at 20° C., vigorous rinsing with water at 0° C., treatment with vapor of sodium nitrite acidified with hydrochloricacid (mild conditions); the constituents of the mixture and the mixture being prepared ad hoc and the reaction being performed at 0° C., vigorous rinsing with a coupling buffer, grafting of the antibody-poly-L-lysine mixture; the poly-L-lysine coupled to the antibody-latex in this manner has a saturation effect on the grafting sites (—CON3), and stabilizes the reactant sterically during its storage; the proportions of antibody and poly-L-lysine vary depending on the desired enrichment in antibody on the synthetic microsphere and depending on whether it is intended to employ the right-hand or left-hand portion in relation to the equivalence point of the curve shown in FIG. 1; it should be noted that the method according to the invention permits the use both of the right-hand portion and of the left-hand portion of the said curve, desorption of the antibodies fixed by ionic bonding (3M KCl for 15 minutes), and by hydrophobic bounding (KSCN 1M, for 10 minutes)

rinsing storage.

It is obvious that when the functional groups of the particles are —CONH2 (example 169 and 181) or —COOCH3, the hydrazine stage represents the first stage of the grafting process.

The following stage corresponds to the microsphere agglutination stage and this can be done according to the following manner. The latex microspheres are subjected to a periodic circular motion at a frequency of 20 hertz and with an amplitude of 4 mm, this being for a period of ten minutes. This stage is performed at ambient temperature, resulting in a significant reduction in the apparatus (no water bath or heating apparatus of any other type). Performed in this manner, this agglutination stage permits a large decrease in the nonspecific agglutination of the particles. In fact, its efficiency for the nonspecific agglutination of the particles is very high: when one of the methods described earlier, that is to say at 37° C., for one half hour in a water bath with conventional agitation, is employed, nonspecific agglutination is of the order of 30 to 40%. The nonspecific agglutination according to the method described in the invention varies only from 2 to 5%.

Furthermore, this method does not require the particles to be stabilized with bovine albumin or any other ionic agent made electronegative or electropositive at highly basic or highly acidic pH values, which are incompatible with the storage of the reactants.

Consequently, the method makes it therefore possible to maintain the reactant and the calibration ranges at physiological pH values (near 7), thus ensuring very good integrity and excellent storage of the constituents. It should be noted that another advantage which exists lies in avoiding the use of proteinic stabilizing substances, as permitted by the method. In fact, proteinic stabilizing substances, such as albumin, are a source of bacterial contamination, and this is very inconvenient in an industrial reactant which needs to be stored for several months.

Furthermore, the above method permits a marked increase in the specific immunological agglutination of the particles simultaneously with a very marked decrease in the nonspecific agglutination of the particles, and this is also an advantage of the invention.

A saturation plateau in the immunological agglutination of the microspheres is quickly reached in approximately ten minutes. Such a short incubation period, in addition to being highly advantageous for the user who obtains an assay result extremely rapidly, does not, furthermore, involve any particularly painstaking stopwatch timing during the initial addition of the reactant or during the stage when the reaction is stopped.

Furthermore, the efficiency of the method according to the invention in respect of the specific agglutination is such that the agitation may be performed at ambient temperature, and, as already said, this avoids the use of heating apparatus or of water baths, which is an undoubted and appreciable gain in convenience.

According to the invention, it has thus been verified by experiment that nonspecific agglutination, which is associated with weak interactions between the particles (bonding of the ionic, hydrogen or van der Waals type) is made impossible or is highly inhibited by a periodic motion imparted to it, of very low amplitude and very high frequency, whatever the trajectory of the periodic motion (for example, and conveniently, rectilinear, circular or ovalized). It has also been verified that a method such as this markedly promotes the specific (immunological) agglutination of the synthetic microspheres carrying the antigen or the antibody, in the presence of the corresponding antigen or antibody, and thus permits a specific reaction which is rapid and is performed at ambient temperature.

When the agglutination stage has been performed, the incubation medium containing the said microspheres is diluted with water to a volume of around 1 to 4 milliliters.

This dilution can be performed by either water, saline solution or any suitable buffer solution.

This volume corresponds, in fact, to that of a conventional spectrophotometry cell 1 × 1 cm in size.

Figure 2:
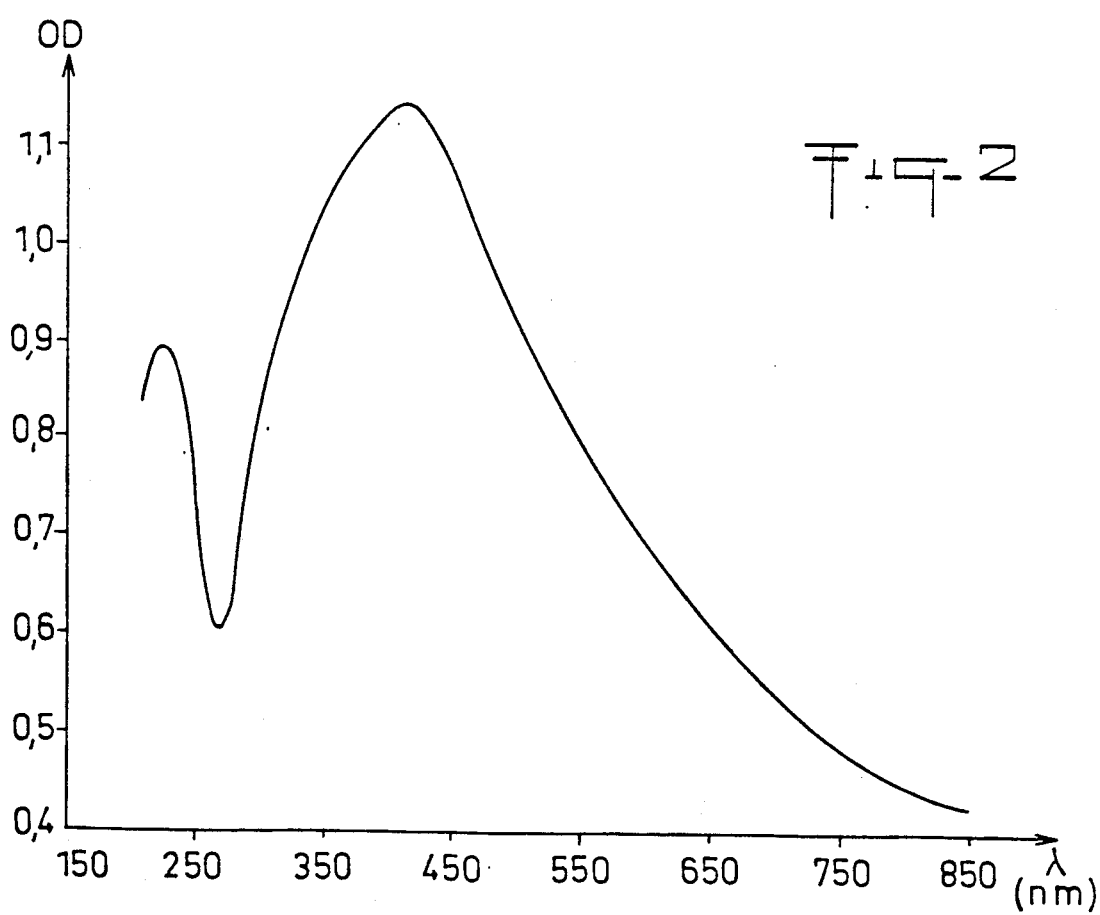
FIG. 2 is a diagram illustrating the ultraviolet and visible absorption spectrum of an aqueous suspension of (nonagglutinated) micrometers of (colourless) polystyrene 0.8 micrometers in diameter.

The reading and measurement stage is then performed. This can be done according in the following manner. In fact, before the agglutination stage as such, the ultraviolet and visible absorption spectrum of an aqueous suspension of the colorless nonagglutinated polystyrene microspheres is obtained in order to determine the absorption maximum of ultraviolet and visible light by these particles; the wavelength representing this absorption maximum is called λmax. It has been shown that the absorption maximum λmax characteristic of a given natural or synthetic microsphere is identical, whether the said microsphere is uncoated or coated with an antibody or antigen molecule. By way of example, FIG. 2 shows the absorption maximum in the ultraviolet and visible region of a concentrated suspension of microspheres of colorless polystyrene with a diameter of 0.8 micrometers, the spectrum being identical when the microspheres are uncoated or coated with an antibody or antigen. However, we can notice that the peak of absorption maximum is a bit flattened because of the interference with the Mie law (intensity of the scattered light forward).

With this wavelength λmax determined in this manner, after the immunological agglutination stage, reading of the result by means of ultraviolet and visible absorption spectrophotometry is performed by working in the vicinity of the said wavelength λmax, determined earlier. In the example described, λmax has a value of 380 nanometers.

Experience shows that the results obtained in this manner according to the invention, by ultraviolet and visible absorption spectrophotometry, show only the absorption of the monomers of the microspheres, the peak amplitude (degree of absorption—optical density—percentage transmission) being proportional to the concentration of the monomeric microspheres in the medium (Beer-Lambert law).

Now, it is already known in an assay of this type that, once the immunological agglutination reaction is complete, the concentration of residual nonagglutinated monomers is proportional to the logarithm of the initial concentration of antigen in the medium.

The result of the reading of the reaction by ultraviolet and visible absorption spectrophotometry in the vicinity of the λmax of absorption of the monomers of the nonagglutinated microspheres is thus also proportional to the logarithm of the initial concentration of antigen in the medium.

It should be noted that this method can be employed whatever the nature of the polymer (especially those listed earlier), and whatever the size of the particles or their color. When the latex particles are colored, the reading can be taken either at the max of the particle or at the λmax of its color. In fact, in the case of the colored latices, the ultraviolet and visible absorption spectra show two peaks, one corresponding to the substance (independent of the color), the other corresponding to the colorant of this substance.

Figure 5:
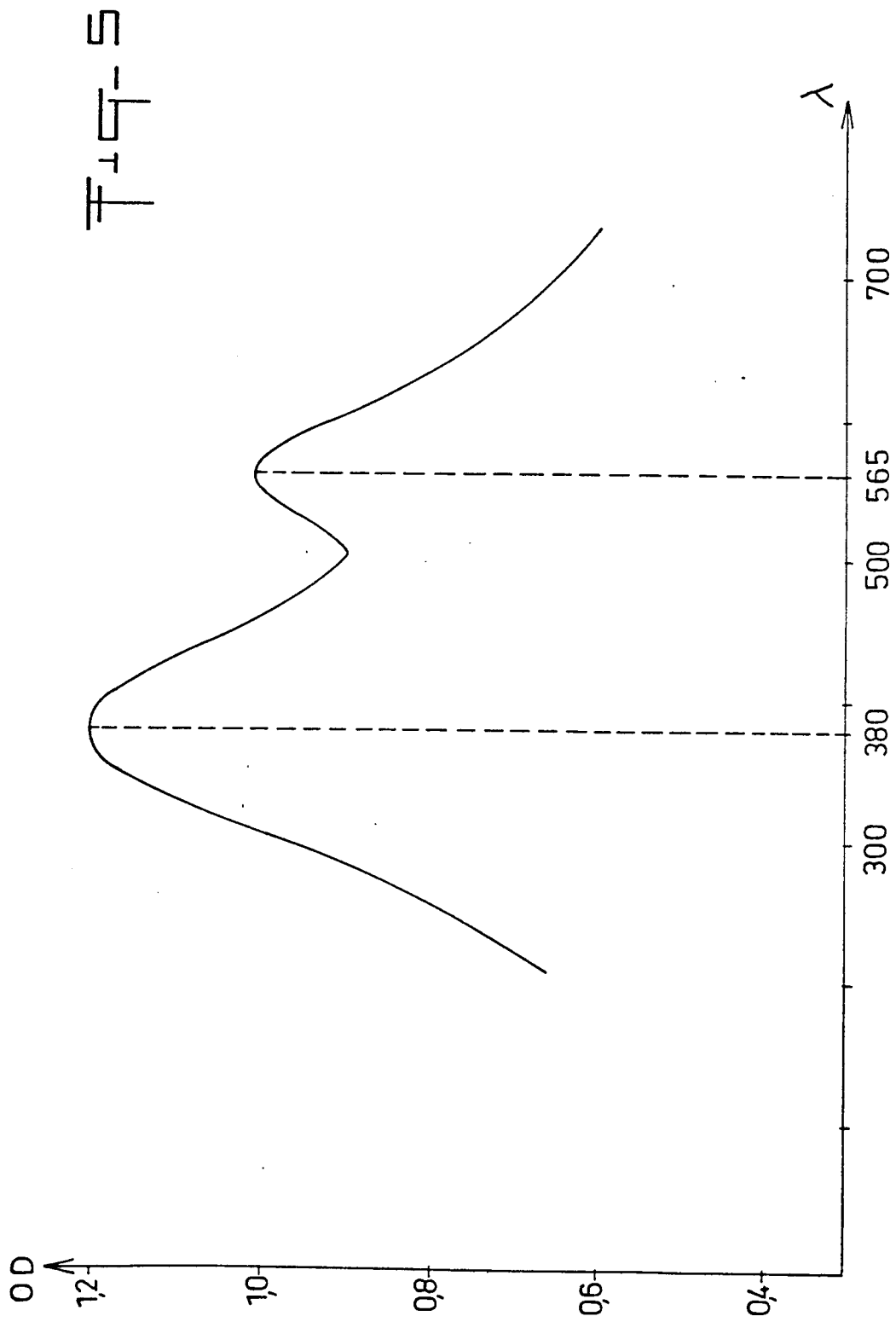
FIG. 5 is a diagram illustrating the ultraviolet and visible absorption spectrum of an aqueous suspension of red polystyrene microspheres 0.8 micrometers in diameter.

This is illustrated in FIG. 5 which shows two peaks in the absorption spectrum of a suspension of red polystyrene microparticles 0.8 micrometers in diameter. The first peak, at 380 nm, corresponds to the absorption maximum of the substance of the microparticles. The second peak, at 560 nm for the red microparticles, corresponds to absorption maximum of the colorant of this substance.

Figure 6:
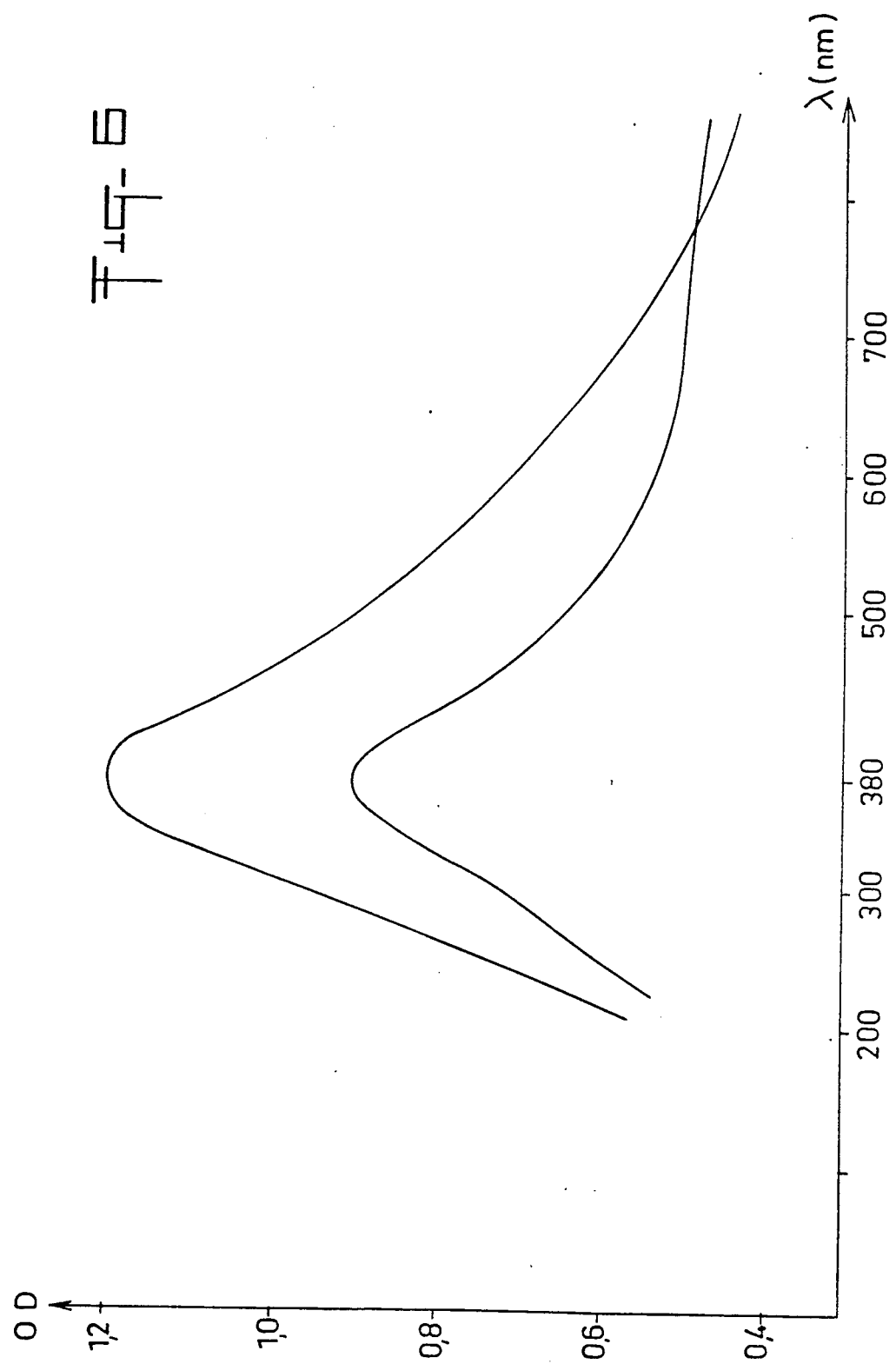
FIG. 6 is a diagram illustrating the ultraviolet and visible absorption spectra of an aqueous suspension of colorless and yellow polystyrene microspheres 0.8 micrometers in diameter, and with the same concentration of microspheres in the two cases.

This phenomenon can be used to obtain an additive effect. This is illustrated in FIG. 6 which shows the ultraviolet and visible absorption spectra of a suspension colorless and yellow polystyrene microspheres 0.8 micrometers in diameter.

The concentration of the microspheres is the same for the two spectra.

The spectrum of the colourless microspheres show a peak at 380 nm, which is the absorption maximum of the substance of the microspheres.

The spectrum of the yellow microspheres also show a peak at 380 nm, but this peak is higher than the latter. It is known that the absorption maximum of a yellow colorant is at about 380 nm. Thus, in this case, there is an additive effect between the absorption maximum of the substance of the microspheres and the absorption maximum of the colorant of the substance.

This additive effect allows increasing in accuracy of the assay.

In practical implementation of the method, it is advantageous to choose a synthetic polymer microsphere whose nature, size or color has an ultraviolet and visible absorption maximum at wavelengths which do not interfere with obstructing wavelengths, especially at 280 nanometers, corresponding to the protein absorption. Advantageously, the method according to the invention employs, for example, carboxylated microspheres of colorless polystyrene with a diameter of the order of 0.8 micrometers, whose ultraviolet and visible absorption maximum is at about 380 nanometers, as already stated. Furthermore, this wavelength does not, in fact, interfere, and thus not with the protein absorption maximum situated at 280 nanometers. This wavelength of 380 nanometers may be selected by means of any spectrophotometer or photometer, regardless of whether an ultraviolet or visible lamp is employed, bearing in mind that the value of 380 nanometers is situated on the borderline between the ultraviolet and the visible. Furthermore, the reading at 380 nanometers in the visible is within the range of any laboratory photometric or spectrophotometric apparatus, resulting in a major simplification of the apparatus required for the assay method.

Figure 3:
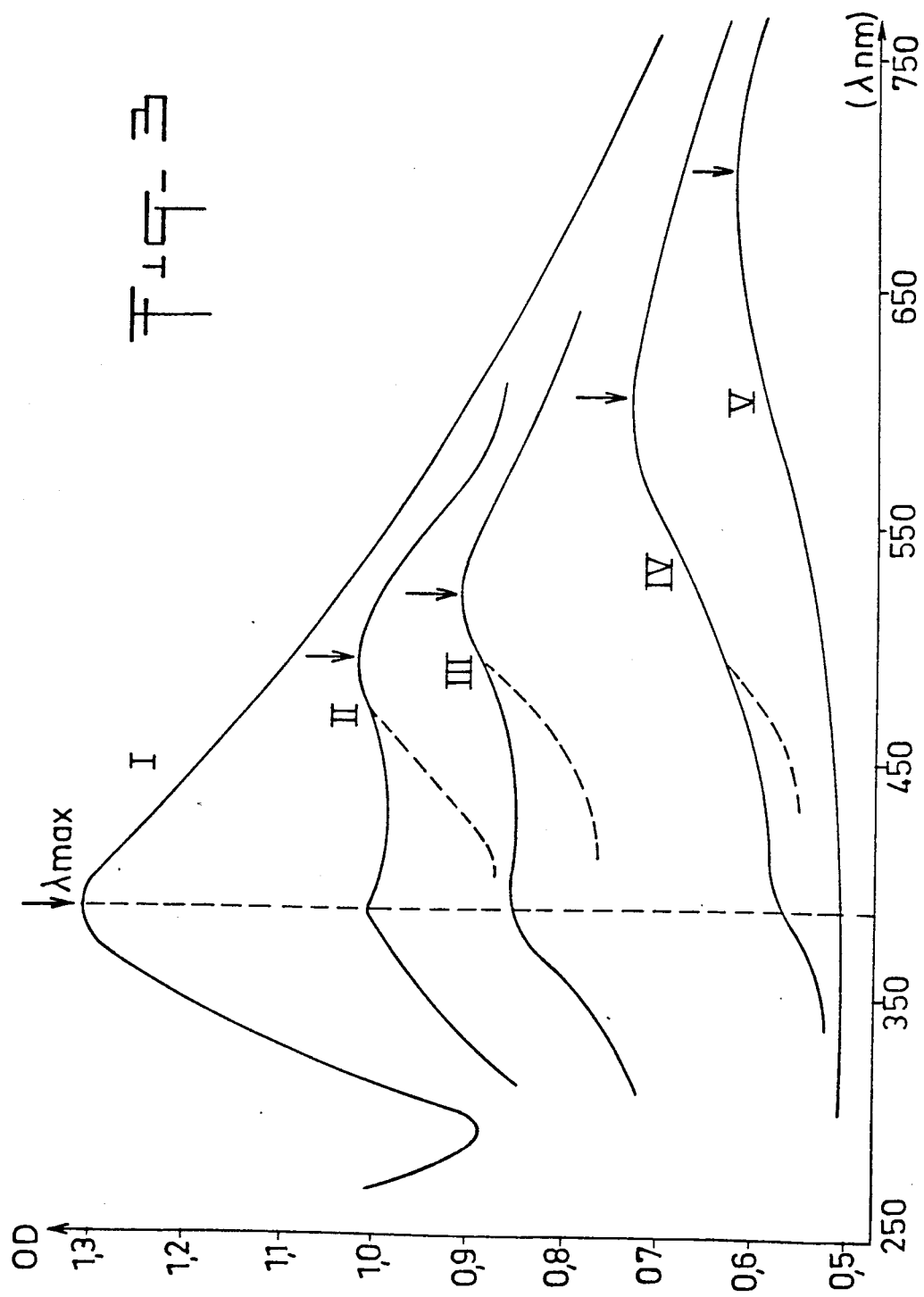
FIG. 3 is a diagram illustrating the ultraviolet and visible absorption spectra of (colourless) antibody polystyrene microspheres 0.8 micrometers in diameter, nonagglutinated (curve I), and agglutinated by means of increasing concentrations of 50 nanograms/milliliter (curve II), 100 nanograms/milliliter (curve III), 500 nanograms/milliliter (curve IV) and 1 microgram/milliliter (curve V) of the corresponding antigen.

Furthermore, experience shows that the absorption maximum λmax is characteristic of the deagglutinated microspheres and that agglutinates of these same microspheres no longer absorb at this maximum, even when they are very small in size. It has been observed, in fact, that aggregates of synthetic microspheres of polymers have an absorption maximum which is characteristic of their size. It has also been observed that the agglutinates have an absorption maximum which is proportionately shifted towards longer wavelengths the larger their size. FIG. 3 shows (arrows) the absorption maximum of colorless microspheres of antibody polystyrene (0.8 micrometers in diameter), nonagglutinated, and the absorption maxima of the agglutinates of increasing size of these same microspheres. It shows:

on one hand, the absorption of the residual microspheres not agglutinated by the antigen (at λmax), and on the other hand, the absorption of the aggregates of increasing size, induced by increasing antigen concentrations.

From the preceding it clearly follows that if the reading of a solution containing a mixture of monomeric microspheres and of their agglutinates is performed by ultraviolet and visible absorption spectrophotometry, operating at a wavelength which corresponds to the λmax of absorption of the nonagglutinated (monomeric) microspheres, then the measurement performed in this manner will relate to and hence will detect only the monomers of the particles, because only they absorb at this maximum.

This novel reading method, according to the invention, has many advantages when compared with the state of the art described earlier:

it does not require the use of very sophisticated and costly apparatus such as particle counters, laser nephelometers or infrared opacimeters, in contrast to turbidimetric techniques in the visible, it can be employed with very high particle concentrations in the incubation medium, and this endows the assay with very high precision, which is impossible to obtain in visible or near infrared turbidimetry (opacimetry). By way of example, Table I below gives the optical densities obtained by spectrophotometric reading of ultraviolet and visible absorption of the result produced by the agglutination of colorless microspheres of antibody polystyrene 0.8 micrometers in diameter, for two very low concentrations of the corresponding antigen

TABLE I

| Initial concentration of antigen | 10 ng/ml | 1 μg/ml |
|---|---|---|
| optical density, UV and visible absorption at 380 nm | 1.3 | 0.5 |

The 380 nm wavelength corresponds to the maximum of the absorption of ultraviolet and visible light by the nonagglutinated monomeric microparticles.

the degree of precision permitted by the reading method according to the invention also permits the use of any spectrophotometer and the use of reading cells of a commonplace model ($1 \times 1$ cm).

The results given in the above Table correspond to a measurement performed by means of a conventional reading cell with a 1 cm optical path. An optical path of 4 centimeters, which is difficult to achieve in practice, would be needed to obtain the same precision using turbidimetry.

In addition to an absorption spectrophotometer of a common type, the device for implementing the method described above comprises a compartmented casing and a means suitable for imparting a vibrational motion to the solution containing the microspheres.

Figure 7:
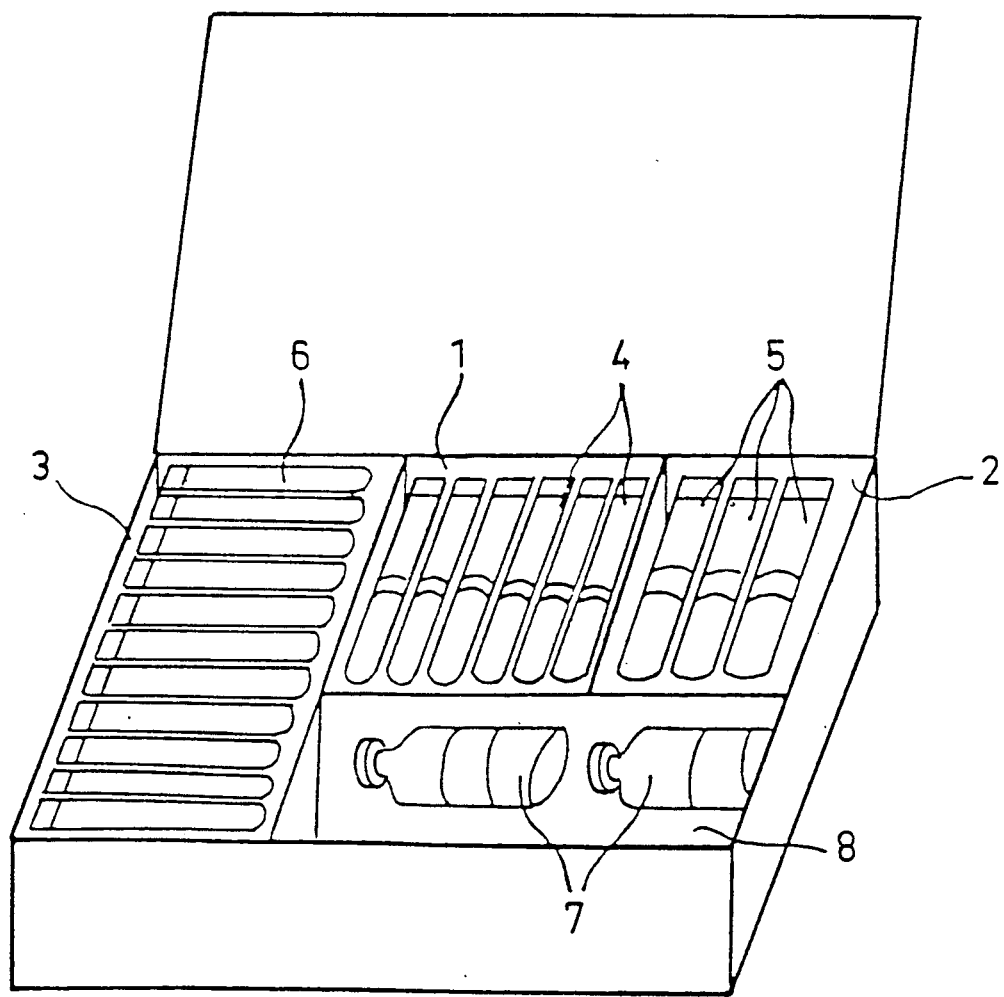
FIG. 7 is a view of a compartmental casing relating to the method for implementing the invention.

The compartmental casing, illustrated in FIG. 7, in the form of a rectangular parallelepiped, is $13 \times 16 \times 4$ cm in size and is made of plastic or of stiff cardboard. It has four compartments:

(1) the first compartment (1) contains a plurality of horizontal and parallel haemolysis tubes (4), which are closed and labelled (marked with the antigen concentration), and containing 2 to 4 calibration ranges in freeze-dried form, (2) the second compartment (2) also contains a plurality of haemolysis tubes (5), but larger in size, horizontal and parallel, and containing the reactant ready for use, in this case the antibodies grafted onto the microspheres, immersed in an appropriate diluent. In fact, the diluent should ensure the preservation of the antibodies, their stability with time and their satisfactory integrity.

These tubes are four in number per standard range, and contain 2.5 milliliters of reactant.* The concentration in weight of the microparticles is comprised between 0.1 and 10 percent and preferably between 1 and 5 percent.

*It is surprising and one main advantage of the invention, that we could proceed with such high concentrations, which were only used with visual qualitative processes readings on glass strips, as described for example in U.S. Pat. No. 4,542,103.

(3) the third compartment (3) contains a plurality of closed, small-diameter tubes (6) containing a specimen of the dilution solution of the calibration range, in freeze-dried form.

The quantity of freeze-dried dilution solution is advantageously the quantity which is necessary to dilute a biological sample, for example the quantity necessary to dilute ten times a biological sample which has already been diluted with distilled water. A quantity of 0.45 ml or 0.9 ml is very suitable.

(4) the fourth compartment (8) contains at least one flask (7) of dilution liquid concentrate.

The means capable of ensuring the periodic motion of the microspheres at high frequency and with low amplitude comprises a motor fixed to a verticle shaft actuating a cam. This cam imparts a periodic motion of high frequency and low amplitude, and with a circular trajectory, to a tray which is itself fixed to a support for parallel tubes. The said tray, of elongate overall shape, remains always parallel to its original direction. The means capable of ensuring the periodic motion also comprises a chassis on which the display of the motor rotation speed and the start-up are adjusted. The amplitude of the motion is limited in the present case to 4 mm and the frequency displayed is 20 hertz.

Thus, when an antigen assay of a solution is to be carried out, for example the assay of $\beta 2$ microglobulin in a renal insufficiency serum, 50 microliters of the serum to be analyzed are first taken and 0.45 ml of distilled water is added to it. A 50 microliter sample is taken from the solution prepared in this manner and is placed in one of the tubes (6) in the compartment (3), made up beforehand with 0.45 ml of distilled water. A conventional homogenization is carried out .05 microliters are then taken from this tube and are mixed with 50 microliters of the reactant ready for use, that is to say the corresponding antibody, grafted onto the microspheres and present in one of the tubes (5) of the compartment (2), and which has been homogenized beforehand. The in weight-concentration of polystyrene microspheres of this reactant is advantageously about 1 percent.

The new solution produced in this manner is placed on the support which is fixed to the tray, which is preferentially already in motion, means ensuring the periodic motion of high frequency and low amplitude. It is subjected to this periodic motion for a period of ten minutes, the frequency of vibration being 20 hertz and the amplitude 4 mm. When this agglutination stage has been performed, the dilution stage takes place. The volume obtained changes from 100 microliters to 3.6 ml, that is to say to the volume corresponding to the spectrophotometric analysis cell. The contents of the tube are then poured into the $1 \times 1$ cm reading cell and a spectrophotometric analysis is carried out at the absorption maximum of the nonagglutinated microspheres in the ultraviolet and visible, in this case at 380 nanometers, that is to say at the borderline between the visible and the ultraviolet. From a practical point of view, the hemolysis tubes can be directly placed in the spectrophotometer. Previously, one of the calibration ranges present in the compartment (1) of the casing has been employed in order to plot the straight line representing the relationship between the optical density and the logarithm of the antigen concentration. Once the optical density of the solution obtained has been determined, it is compared to the calibration curve and the concentration of antigens in the initial serum is deduced therefrom in an extremely strict manner.

Figure 4:
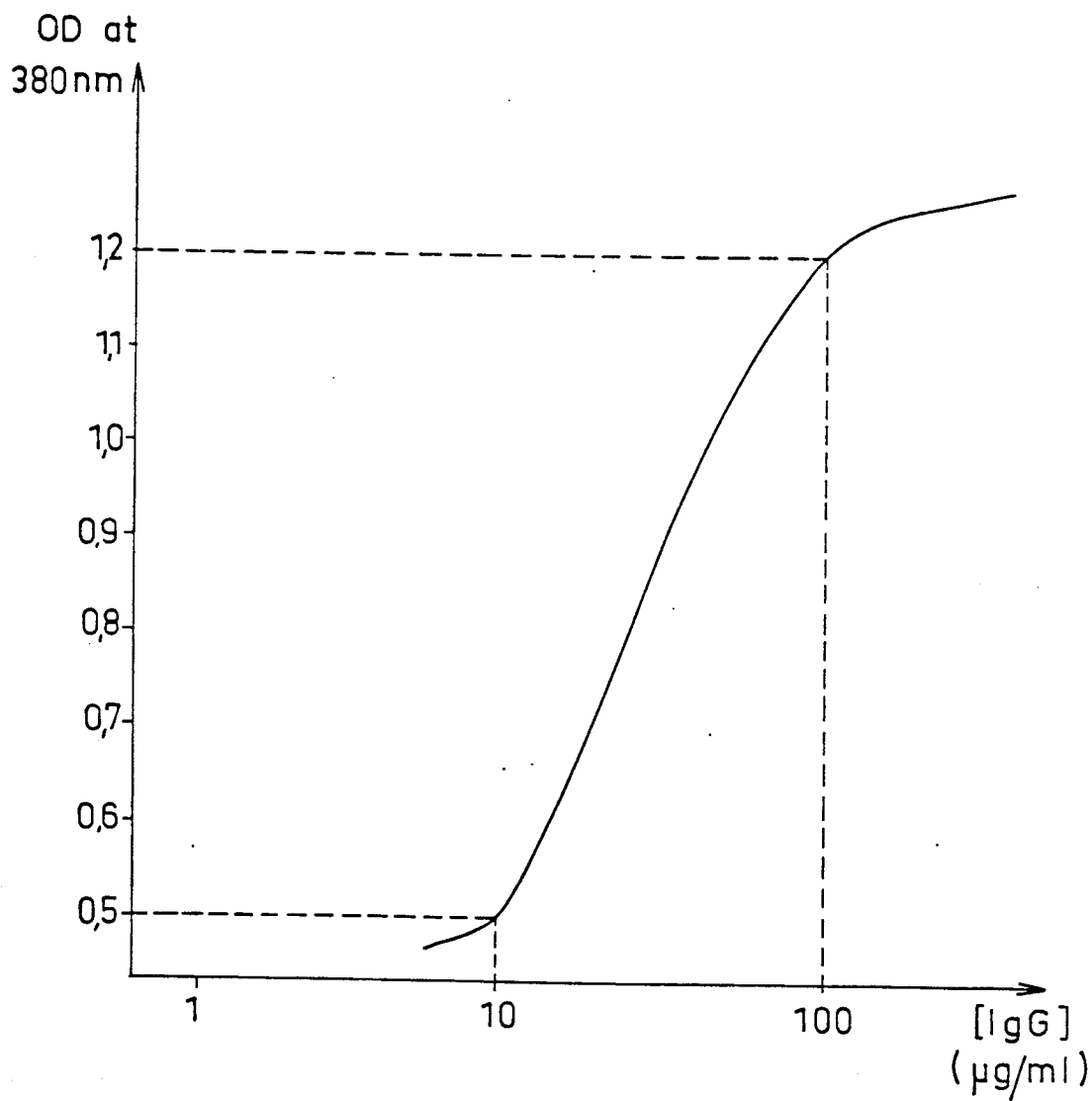
FIG. 4 is a diagram illustrating an assay of human immuno-gamma-globulins G by the method according to the invention.

FIG. 4 is an illustration of an assay of human immuno-gamma-globulins G by means of the method and the device according to the invention. In this example, it is the portion on the right-hand side of the equivalence point of the curve in FIG. 1 which is employed. The coefficient of correlation with laser nephelometry which is obtained for this assay for 100 cephalorachidian liquids and serums is close to 1.

Table II, which follows, is a Table comparing the method according to the invention with a radioimmunotest for the assay of human $\beta 2$ microglobulin in normal and renal-insufficiency serums and in dialysis liquids.

TABLE II

| | concentration of $\beta 2$ microglobulin in ug/ml | | | | | | | |
|---|---|---|---|---|---|---|---|---|
| Method according to the invention | 11.6 | 5.7 | 0.7 | 2.97 | 2.24 | 2.13 | 2.71 | 2.23 |
| radio-immunotest | 13.2 | 6.7 | 0.41 | 2.06 | 2.12 | 2.05 | 2.60 | 2.30 |

In addition to the advantages emphasized earlier, the present invention gives rise to other advantages, among which there may be mentioned:

possible in-situ assay, that is to say at the patient's bedside, a thing which was hitherto made very difficult because of the bulk of the apparatus employed, very high speed of implementation and of determination of the results, together with very high reliability, which makes this method possible in emergency biochemistry or pharmacology, and in following graft survival, the feasibility of analysis throughout the usual ambient temperature region.

This invention is therefore particularly suited for many fields of research and medicine, especially in cancerology, hormonology, endocrinology, clinical biochemistry, toxicology and microbiology.

Furthermore, it is of great interest in the field of pyretogen control in the pharmaceutical industry and in that of haemodialysis.

I claim:

1. A method of quantitatively assaying an immunologically reactive substance of clinical interest by means of other substances of the same type, such as an assay of an antigen by means of an antibody and vice versa, said method comprising:

grafting, in a liquid medium, an immunologically active substance, which acts as the assay reactant, onto natural or synthetic microparticles;

radiating said liquid medium, which contains said microparticles, with radiation in the ultraviolet and visible absorption spectrums, to determine the wavelength corresponding to the absorption maximum of said liquid medium, said wavelength being $\lambda_{max}$;

subjecting said microparticles to an agglutination reaction in said liquid medium with an immunologically reactive substance of clinical interest;

diluting said liquid medium to provide a diluted incubated medium; and optically measuring, via radiation scanning involving absorption spectrophotometry in the vicinity of said $\lambda_{max}$, said diluted incubated medium, to determine the assay of said immunologically reactive substance of clinical interest.

2. The method of claim 1, wherein said microparticles consist of natural or synthetic microparticles which exhibit an absorbing nature, which includes real absorption and any loss of observed light intensity related to said microparticles.

3. The method of claim 1, wherein said microparticles are selected from the group consisting of synthetic polymers of vinyl toluene, acrylonitrile, styrene-butadiene, acrylonitrile-acrylic acid derivatives, acrylic esters, vinylbutadiene and polystyrene.

4. The method of claim 1, wherein said microparticles consist of microspheres.

5. The method of claim 4, wherein said microspheres are calibrated and have a diameter of about 0.01-5.0 microns.

6. The method of claim 4, wherein said microspheres are calibrated and have a diameter of 0.8-1.0 microns.

7. The method of claim 1, wherein said microparticles are colorless.

8. The method of claim 1, wherein said microparticles are colored, and the optical measurement step is performed either at $\lambda_{max}$ or at the wavelength corresponding to the absorption maximum of the color of said colored microparticle.

9. The method of claim 8, wherein the color of the microparticles is selected in order to have an additive effect between $\lambda_{max}$ and the absorption maximum of the color of the microparticle.

10. The method of claim 1, wherein said microparticles are suspended in said liquid medium in an aqueous suspension.

* * * * *